(12) United States Patent
Tsuda et al.

(10) Patent No.: US 7,252,016 B2
(45) Date of Patent: Aug. 7, 2007

(54) INJECTOR

(75) Inventors: Takao Tsuda, 3102, Kaguyama 2-chome, Nisshin-shi, Aichi (JP); Eiji Iizuka, Nagoya (JP); Motonori Munesue, 178-11, Kitashinmachi 6-chome, Matsubara-shi, Osaka (JP)

(73) Assignees: Takao Tsuda, Aichi (JP); Chemco Scientific Co., Ltd., Osaka (JP); Motonori Munesue, Osaka (JP)

( * ) Notice: Subject to any disclaimer, the term of this patent is extended or adjusted under 35 U.S.C. 154(b) by 399 days.

(21) Appl. No.: 10/994,124

(22) Filed: Nov. 19, 2004

(65) Prior Publication Data
US 2005/0118072 A1 Jun. 2, 2005

(30) Foreign Application Priority Data
Nov. 27, 2003 (JP) .............................. 2003-397271

(51) Int. Cl.
*G01N 35/10* (2006.01)
(52) U.S. Cl. .................................... 73/863.01; 250/576
(58) Field of Classification Search ..............................
73/864.83–864.85, 863.01, 864.81, 864.87;
250/576
See application file for complete search history.

(56) References Cited

U.S. PATENT DOCUMENTS

| | | | | |
|---|---|---|---|---|
| 4,710,641 A | * | 12/1987 | Aulds et al. ................ | 250/554 |
| 5,059,025 A | * | 10/1991 | Ando ......................... | 356/319 |
| 5,651,614 A | * | 7/1997 | Juneau ........................ | 374/17 |
| 5,930,033 A | * | 7/1999 | Inoue et al. ................ | 359/368 |
| 6,992,759 B2 | * | 1/2006 | Nakayama et al. ......... | 356/244 |
| 2002/0112530 A1 | * | 8/2002 | Kitagawa ............. | 73/863.01 X |
| 2003/0148536 A1 | * | 8/2003 | Liang et al. ................ | 436/172 |

FOREIGN PATENT DOCUMENTS

| | | | | |
|---|---|---|---|---|
| JP | 61275639 A | * | 12/1986 | ............. 73/863.01 |
| JP | 2000-186985 A | | 7/2000 | |

* cited by examiner

*Primary Examiner*—Thomas P. Noland
(74) *Attorney, Agent, or Firm*—Akin Gump Strauss Hauer & Feld LLP (57) ABSTRACT

An injector has a sample chamber for retaining a small amount of sample, wherein a position of the sample chamber is controlled by transmitting light through the sample chamber and detecting the transmitted light so as to recognize the position of the sample chamber, and it is possible to reduce detection error compared to the conventional injectors that indirectly control the position of the sample chamber by transmitting light through the light passage which is adjacent to the sample chamber. A method for injecting a sample comprising the steps of: providing an injector which has a sample chamber for retaining a sample with an open month; transmitting light through the sample chamber; detecting the transmitted light so as to recognize a position of the sample chamber; and controlling the position of the sample chamber by using the detection result to connect the open month of the sample chamber to an open month of a sample receiving member in order to inject the sample into the sample receiving member.

1 Claim, 7 Drawing Sheets

PRIOR ART

INJECTOR

BACKGROUND OF THE INVENTION

This invention relates to an injector, for example, in a rotary type, especially used in chromatography.

Japanese Patent Application Publication Laid-Open No. 2000-186985, the disclosure of which is herein incorporated by reference, discloses a micro-injector which is generally used in liquid chromatography.

Figure 7:
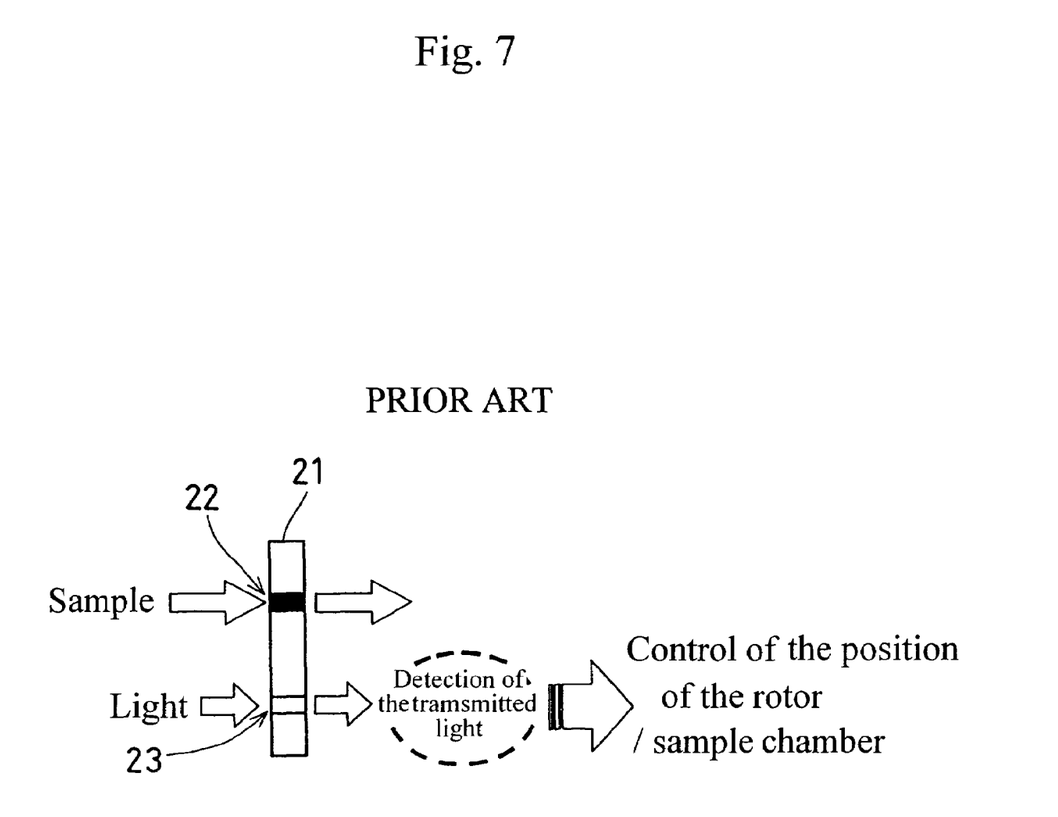
FIG. 7 is a diagrammatic illustration demonstrating an injector of the prior art which is a rotor.

As shown in FIG. 7, the above type of injector which is a rotor 21 includes a sample chamber 22 (a flow channel) for a sample eluent to pass through and a light passage 23, both of which are provided in the rotor 21. The position of the sample chamber 22 is recognized by transmitting light through the light passage 23 and detecting the transmitted light with a light-detector, and thus the position of the sample chamber 22 is indirectly controlled.

However, since the internal diameter of the sample chamber 22 is so small, it is required to control the position of the sample chamber 22 with accuracy down to the micrometer in order to connect the sample chamber 22 to an open mouth of a capillary column at the downstream end of the sample chamber 22.

Therefore, an object of the present invention is to provide an injector that has an accurately position-controllable sample chamber.

SUMMARY OF THE INVENTION

The present invention provides an injector having the following technical features to achieve the above object.

(1) An injector according to the present invention has a sample chamber for retaining a small amount of sample, wherein a position of the sample chamber is directly controlled by transmitting light through the sample chamber and detecting the transmitted light so as to recognize the position of the sample chamber.

In this injector, since the position of the sample chamber is directly controlled by transmitting light through the sample chamber and detecting the transmitted light, it is possible to reduce detection error compared to the conventional injectors that indirectly control the position of the sample chamber by transmitting light through the light passage which is adjacent to the sample chamber.

(2) The above injector may be a rotor (a rotary type injector), wherein the sample chamber is provided in the rotor and the rotation of the rotor is controlled by transmitting light through the sample chamber and detecting the transmitted light so as to recognize the position of the sample chamber.

This feature allows a smooth operation of the rotary type injector because the sample chamber is provided in the rotor.

(3) The above injector may further have an optical transparent capillary tube and the sample chamber may be provided in the capillary tube.

This feature allows more amount of light transmission through the sample chamber because, when light comes into the sample chamber, the light is transmitted through not only a hollow portion of the capillary tube (the sample chamber) which the sample flows through but also the capillary tube itself. Since the amount of light transmitted through the sample chamber is increased, it becomes easier to detect the light transmitted through the sample chamber.

(4) As the optical transparent capillary tube, a fused silica capillary tube may be used.

This feature allows even more amount of light transmission because the fused silica capillary tube, which is made of glass, has better optical transparency than a PEEK tube or the like; so that it becomes possible to carry out better direct control of the position of the sample chamber.

(5) In the above injector, the sample chamber may be connected with a light conducting capillary tube at the upstream end of the sample chamber, wherein the light conducting capillary tube is a polytetrafluoroethylene tube filled with a mixed solution of water and ethanol.

This feature allows efficient irradiation of light to the sample chamber because an optical fiber, which performs superior light conductivity, is formed by having the wall surface of the polytetrafluoroethylene tube as a cladding and the mixed solution as a core.

(6) The above fused silica capillary tube may have an external wall coated with an optical transparent resin.

This feature allows more amount of light transmission to a light-detector afterwards because the resin coated on the external wall of the capillary tube improves the light-transmitting ability of the capillary tube because of its optical transparency.

This fused silica capillary tube with the external wall coated with the optical transparent resin may be used not only as the capillary tube of the sample chamber but also as the capillary column which is connected with the sample chamber at the downstream end.

(7) A stationary phase which is capable of holding a sample may be provided to an internal wall of the above capillary tube.

This feature allows the sample chamber to retain a large amount of sample because the sample is retained not only in the sample solvent which is filled in the sample chamber but also in the stationary phase which is provided to the internal wall of the capillary tube. As the stationary phase, chemically-modified octadecylsilane may be provided to the internal wall of the capillary tube.

(8) The light which is transmitted through the sample chamber may be a laser light. The laser light allows more accurate control of the position of the sample chamber because it has stronger light intensity.

(9) The above stationary phase may be made so as to release the sample which is held thereon as the temperature of the sample chamber is increased by the light which is used to recognize the position of the sample chamber.

Since the capillary tube is heated up when it receives light, the sample which is held on the stationary phase (e.g. octadecylsilane) can be released therefrom. Therefore, the light transmitted through the capillary tube can be used to recognize the position of the sample chamber, and at the same time, can also be used to release the sample from the stationary phase, and this makes it possible for the sample chamber to retain a large amount of sample in the space thereof.

The present invention composed as above has the following effects.

An injector according to the present invention can control the position of the sample chamber by transmitting light directly through the sample chamber and detecting the transmitted light so as to recognize the position of the sample chamber, so that it is possible to reduce detection error and allow more accurate control of the position of the sample compared to the conventional injectors.

DETAILED DESCRIPTION OF THE INVENTION

Referring to Figures, the following description will discuss embodiments of the present invention.

As shown in FIGS. 1-6, in a rotary type injector 1 of this embodiment according to the present invention, a laser light (a light ray) which is generated by a laser generator 2 is transmitted into a sample chamber 7 (a sample flow channel) through a lens 3, an optical fiber 4, a three-way connector 5 and a light conducting capillary tube 6a, and then the laser light reaches to a capillary column 8. The sample chamber 7 is provided in an optical transparent capillary tube 6b. A small amount of sample is supplied into the sample chamber 7 by a constant pressure pump 9 through the three-way connector 5.

Figure 1:
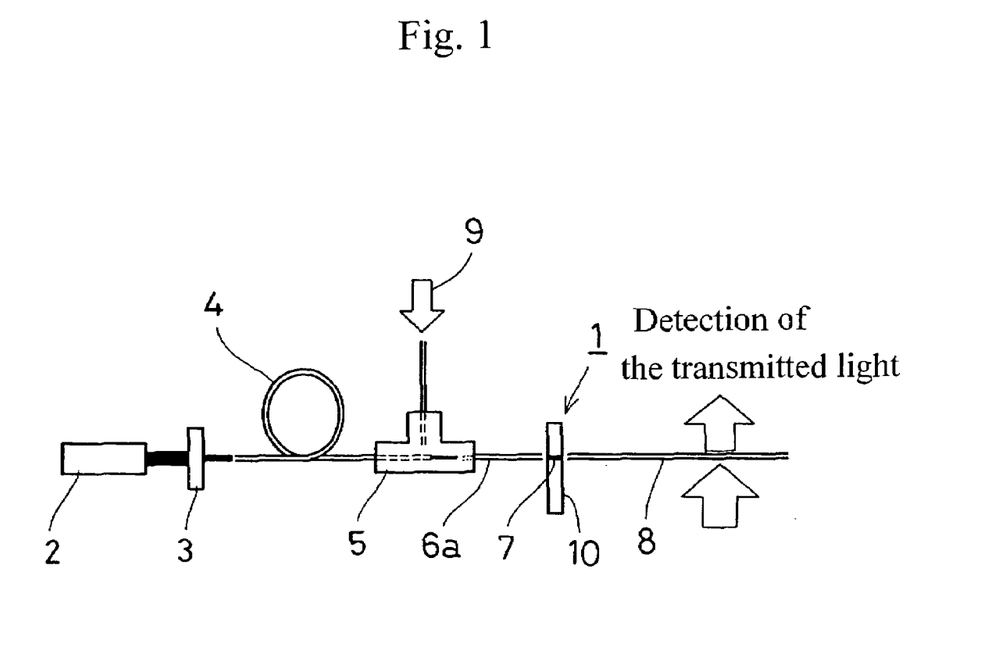
FIG. 1 is a diagrammatic illustration demonstrating a system including an injector which is a rotor according to the present invention.
Figure 2:
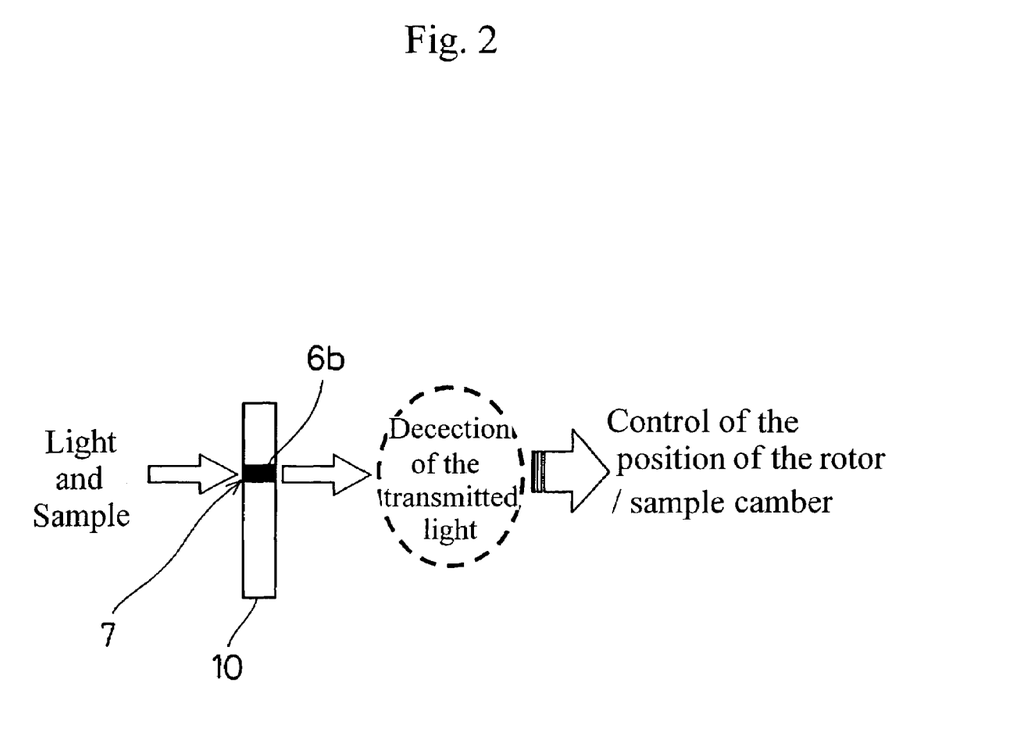
FIG. 2 is a diagrammatic illustration demonstrating the injector shown in FIG. 1.
Figure 3:
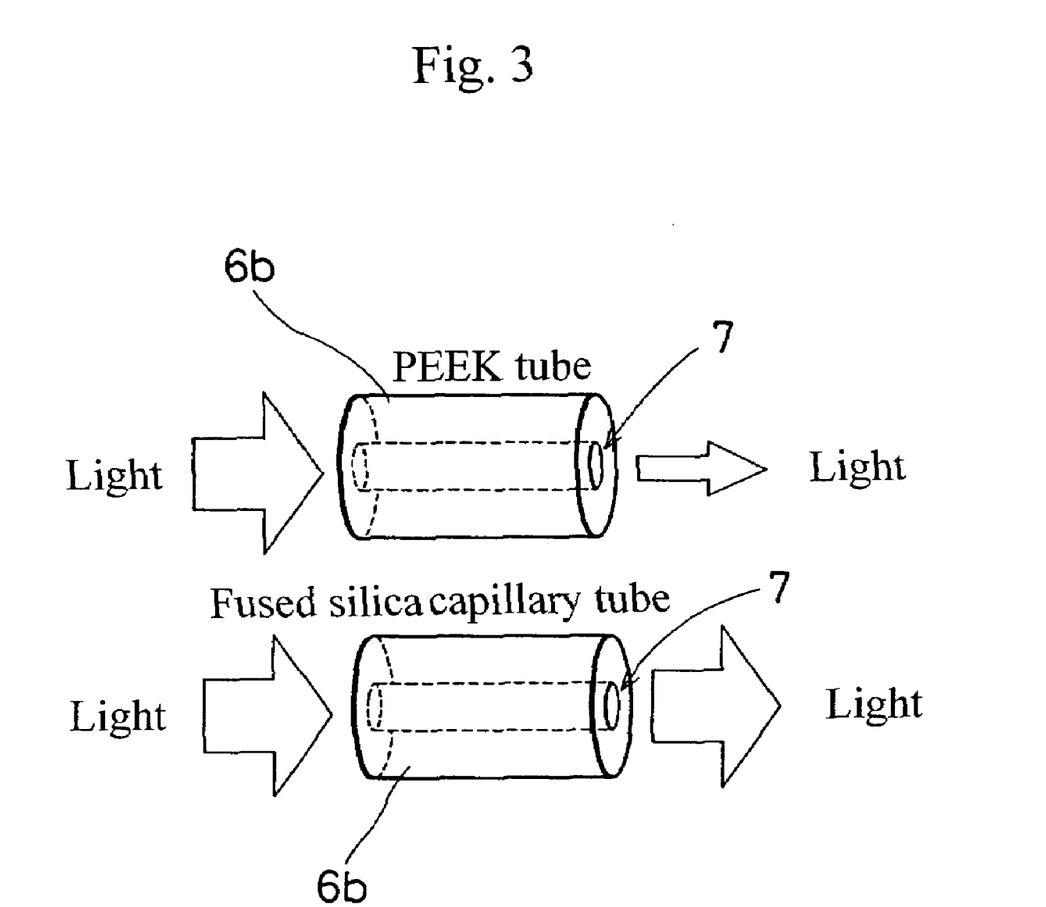
FIG. 3 is a diagrammatic illustration demonstrating a difference between the amount of light respectively transmitted through sample chambers of capillary tubes made of different materials.

As shown in FIGS. 1 and 2, the rotary type injector 1 (the rotor 10) includes the capillary tube 6b, and the sample chamber 7 in which a small amount of sample is retained. As shown in FIGS. 2 and 3, the sample chamber 7 is provided in the capillary tube 6b which is a hollow capillary tube and has optical transparency.

Instead of using the optical transparent capillary tube as the capillary tube 6b provided in the injector 1, it is more preferable to use a fused silica capillary tube an external wall of which is coated with an ultraviolet radiation transmission resin (an optical transparent resin).

An internal wall of the fused silica capillary tube may be provided with a silica gel fixed thereto, and the silica gel may be chemically modified by octadecylsilane.

As shown in FIGS. 2 and 3, the position of the rotor 10 having the sample chamber 7 is controlled by recognizing the position of the sample chamber 7 by transmitting laser light through the sample chamber 7 and detecting the transmitted laser light. The sample chamber 7 functions as a passage for both the laser light and the eluant (the small amount of sample) to pass through.

The fused silica capillary tube, the external wall of which is coated with an ultraviolet radiation transmission resin (an optical transparent resin), is also used as the capillary column 8 which is connected with the downstream end of the sample chamber 7. However, CElect™-UVT (trademark), which is made of an optical transparent resin, may be used as the capillary column 8 instead.

A polytetrafluoroethylene tube (a light refractive index of 1.29) which is filled with a mixed solution of water (a light refractive index of 1.333) and ethanol (a light refractive index of 1.359) is used as the light conducting capillary tube 6a which is connected with the upstream end of the sample chamber 7. If the water and the ethanol are mixed at the rate of approximately 50:50 to make the mixed solution, more amount of light is transmitted through the light conducting capillary tube 6a. For example, Teflon® may be used as the polytetrafluoroethylene.

Next, usage of the rotary type injector of this embodiment is described below.

In this rotary type injector 1, the optical transparent capillary tube 6b provides the sample chamber 7 for retaining a small amount of sample. The position of the sample chamber 7 (the rotation of the rotor 10) is controlled by recognizing the position of the sample chamber 7 by transmitting laser light through the sample chamber 7 and detecting the transmitted laser light. When light comes into the capillary tube 6b, the light is transmitted through the wall portion of the capillary tube 6b as well as the hollow portion of the capillary tube 6b which the sample flows through because the capillary tube 6b is made of the material which has optical transparency.

Therefore, as shown in FIGS. 2 and 3, because the capillary tube 6b has optical transparency, more amount of light can be transmitted through the sample chamber 7, and this makes it easier to detect the light transmitted through the sample chamber 7. Consequently, the position of the sample chamber 7 can be controlled directly and even more accurately by detecting the light transmitted through the sample chamber 7, compared to the conventional injector which indirectly controls the sample chamber 22 by transmitting light through the light passage 23 which is adjacent to the sample chamber 7 and detecting the transmitted light as shown in FIG. 7.

As shown in FIG. 3, if a fused silica capillary tube is used as the capillary tube 6b, it shows more optical transparency than a polyetheretherketone (PEEK) tube because it is made of glass. Therefore, more amount of light can be transmitted through the sample chamber 7, and the direct control of the position of the injector can be carried out even more accurately.

Furthermore, if the external wall of the fused silica capillary is coated with an ultraviolet radiation transmission resin (an optical transparent resin), the fused silica capillary has a better light-transmitting ability and allows more amount of light transmission to a light-detector.

Additionally, if the polytetrafluoroethylene tube (a light refractive index of 1.29) which is filled with the mixed solution of water (a light refractive index of 1.333) and ethanol (a light refractive index of 1.359) is used as the light-conducting capillary tube 6a which is connected with the injector at the upstream end of the sample chamber 7, it is possible to form an optical fiber by having the wall surface of the polytetrafluoroethylene tube as a cladding and the mixed solution as a core, and the light-conducting capillary tube 6a has an excellent light transmitting ability so as to transmit light to the sample chamber 7 efficiently.

EXAMPLE 1

The detailed structure of the present invention is described below.

To evaluate difference in an amount of the light transmitted through the sample chamber 7 when different materials are used as the capillary tube 6b provided in the rotor 10 as shown in FIGS. 1-3, a PEEK tube and a fused silica capillary tube were selected for the capillary tube 6b in this example.

A laser light (a wavelength of 650 to 700 nm) which was generated by the laser generator 2 was condensed by the lens 3 and then transmitted to the three-way joint 5 through the optical fiber 4. The laser light was further transmitted through the light-conducting capillary tube 6a and entered into the sample chamber 7 having an internal diameter of 50 to 100 μm provided in the capillary tube 6b, and finally the transmitted laser light was detected by the light-detector.

The stationary phase, such as octadecylsilane, which is provided to the sample chamber 7 is heated up by the transmitted laser light so that the sample held on the stationary phase can be released therefrom. Specifically, methyl benzoate, used as the sample in this example, which had been held on the stationary phase, was released from the stationary phase as a result of temperature-rise of the sample chamber 7.

As described above, if the fused silica capillary tube was used as the capillary tube 6b for the sample chamber 7, the amount of the transmitted laser light was increased; therefore, the fused silica capillary tube was suitable for transmitting light. This may be because the fused silica capillary tube is made of glass and the light transmitted through both the hollow portion of the fused silica capillary tube (the sample chamber 7) and the glass wall or glass portion of the tube itself. Therefore, it is effective for the rotary type injector 1 in terms of the direct control of the position that a glass tube having superior optical transparency such as the fused silica capillary tube is selected as the capillary tube 6b for the sample chamber 7.

EXAMPLE 2

Figure 4:
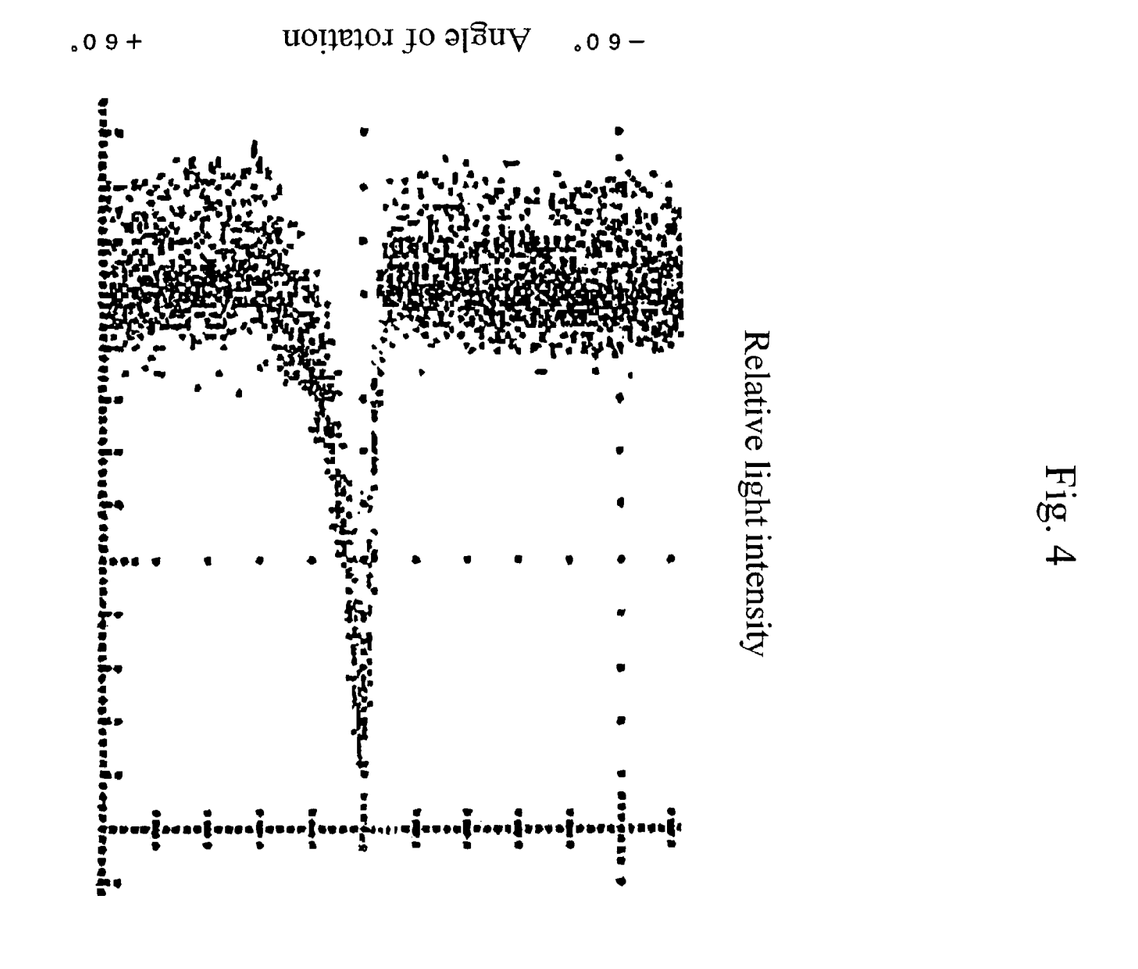
FIG. 4 is a graph demonstrating a relationship between an angle of rotation of a rotor and relative intensity of light transmitted through a sample chamber according to the present invention.
Figure 5:
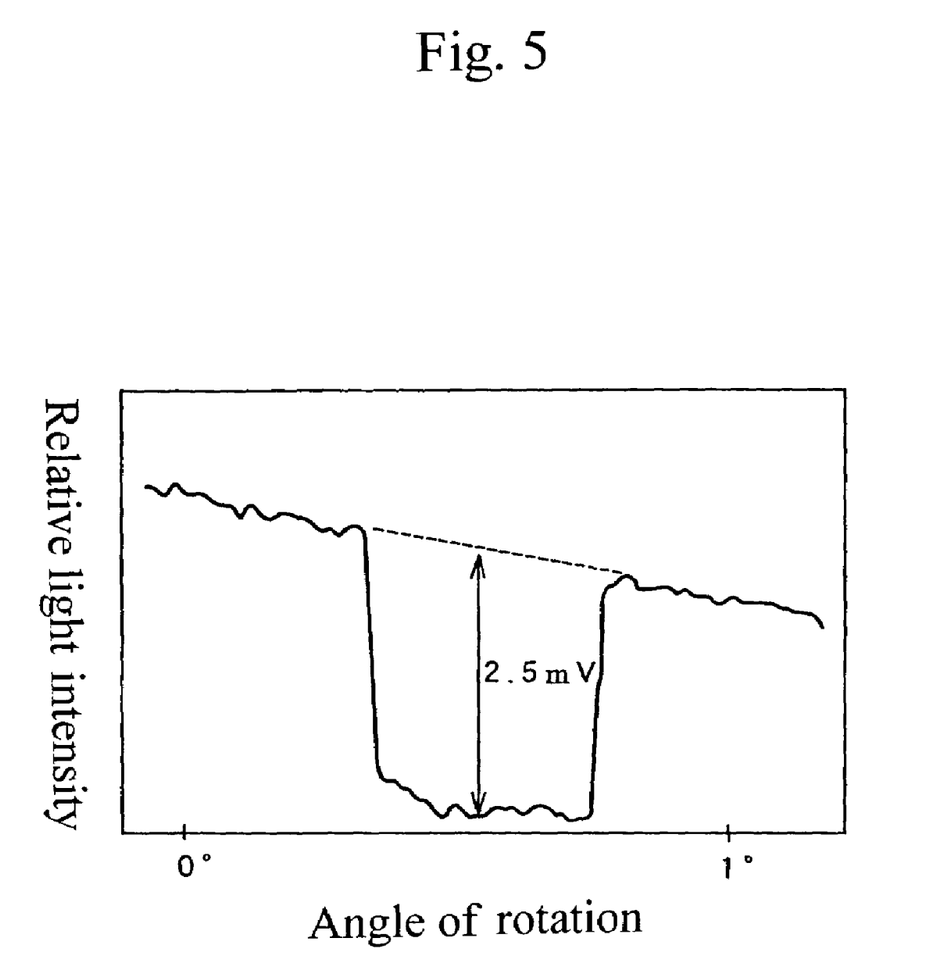
FIG. 5 is a graph demonstrating a relationship between an angle of rotation of a rotor and relative intensity of light transmitted through a sample chamber of a fused silica capillary tube according to the present invention.
Figure 6:
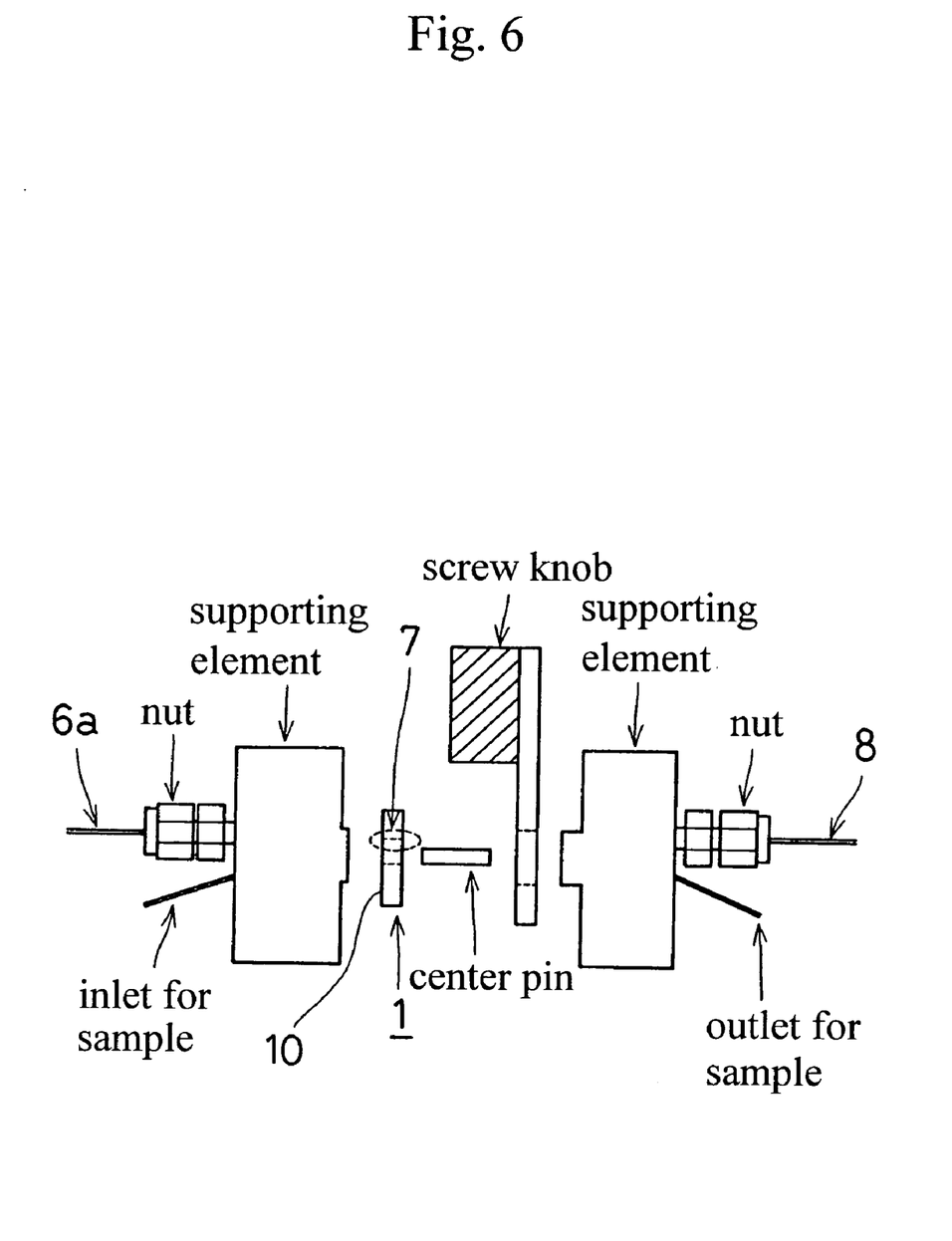
FIG. 6 is a diagrammatic illustration demonstrating a system including an injector for injecting a small amount of sample according to the present invention.

An angle of the rotor 10 showing a predetermined amount of a transmitted light through the sample chamber 7 was measured, and this result was used for controlling the angle of rotation of the rotor 10 accurately.

The sample chamber 7 was provided at a distance of 5.8 mm from the rotational axis of the rotor 10. The diameter of the sample chamber 7 was 100 μm, and the diameter of the column 8 to be connected with the sample chamber 7 was also 100 μm.

FIG. 4 is a graph showing a relationship between an angle of rotation (from −60° to +60°) and an amount of the transmitted light (relative light intensity). FIG. 5 is a graph showing a relationship between an angle of rotation (from 0° to 1°) and a signal corresponding to an amount of the transmitted light (relative light intensity). The signal was converted to "0" when the transmitted light intensity was below the predetermined amount, while the signal was converted to "1" when the transmitted light intensity was above the predetermined amount.

As a result, the rotation error has to be kept 0.05° or less to maintain the displacement of the sample chamber 7 from the corresponding column within 10%. However, if the diameter of the sample chamber and the diameter of the column to be connected to the sample chamber were both 30 μm, the rotation error has to be kept within 0.01° to maintain the above displacement within 10%.

Consequently, the above described structure allows a precise adjustment of the position of the sample chamber 7.

This injector is capable of controlling the position of the sample chamber 7 accurately with less error because the position of the sample chamber is recognized by transmitting light directly through the sample chamber and detecting the transmitted light, so that the injector can be applied for various usage such as a microinjector for liquid chromatography.

It will be appreciated by those skilled in the art that changes could be made to the embodiments described without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for injecting a sample comprising the steps of:
   providing an injector which has a sample chamber for retaining a sample with an open month;
   transmitting light through the sample chamber;
   detecting the light which is transmitted through the sample chamber so as to recognize a position of the sample chamber; and
   controlling the position of the sample chamber by using the detection result to connect the open month of the sample chamber to an open month of a sample receiving member in order to inject the sample into the sample receiving member.

* * * * *